United States Patent [19]
Felix et al.

[11] 3,971,272
[45] July 27, 1976

[54] REGULATION OF ELECTRONICALLY OPERATED QUALITY CONTROL EQUIPMENT

[75] Inventors: Ernst Felix; Hans Locher, both of Uster, Switzerland

[73] Assignee: Zellweger, Ltd., Uster, Switzerland

[22] Filed: July 8, 1974

[21] Appl. No.: 486,600

Related U.S. Application Data

[63] Continuation of Ser. No. 118,100, Feb. 23, 1971, abandoned, which is a continuation of Ser. No. 400,340, Sept. 30, 1964, abandoned.

[30] Foreign Application Priority Data

Oct. 1, 1963 Switzerland.................... 12138/63

[52] U.S. Cl.................................. 83/13; 83/371; 83/365; 324/61 R; 28/64
[51] Int. Cl.²....................... B26D 5/12; B26D 5/38
[58] Field of Search ............... 83/13, 371, 365, 364, 83/361; 324/61; 28/64

[56] References Cited
UNITED STATES PATENTS

| | | | |
|---|---|---|---|
| 3,113,386 | 12/1963 | Hills................................. | 83/371 X |
| 3,122,956 | 3/1964 | Jucker............................. | 83/371 X |
| 3,371,568 | 3/1968 | Felix................................ | 83/13 |
| 3,494,236 | 2/1970 | Kono et al...................... | 83/365 |
| 3,807,270 | 4/1974 | Wirz................................ | 83/371 X |

*Primary Examiner*—Donald R. Schran
*Attorney, Agent, or Firm*—Robert W. Fiddler

[57] ABSTRACT

A method for regulating the operation of yarn clearers having error correcting means such as yarn cutters, and sensing means providing an electrical signal representative of the controlled quality. The method comprises the steps of: feeding the signal from the sensing means to two independent electrical circuit channels each having separate threshold switch means, the threshold switch means of one circuit responsive to signals corresponding to yarn faults of given magnitude. The threshold switch means of the other circuit responds to signals corresponding to faults of given duration. Thereafter, an independent control signal is obtained from each of said channels for initiating the operation of the cutters when a limiting value selected for each of said two channels is exceeded.

5 Claims, 5 Drawing Figures

INVENTORS
ERNST FELIX
HANS LOCHER
BY
Robert W. Eddy

INVENTORS
ERNST FELIX
HANS LOCHER
BY

ATTORNEY.

REGULATION OF ELECTRONICALLY OPERATED QUALITY CONTROL EQUIPMENT

This application is a continuation of application Ser. No. 118,100, filed Feb. 23, 1971, now abandoned which is a continuation of Ser. No. 400,340, filed Sept. 30, 1964, now abandoned.

This invention relates to the art of quality control, more particularly to the regulation of electronically operated quality control equipment such as yarn cleaners, or the like so that the quality control equipment may be selectively adjusted to eliminate faults of a given magnitude only when they occur over an undesired period.

A variety of situations exist in which quality control equipment is employed in conjunction with production systems to insure that the production systems are operating as desired. The quality control equipment generally comprises means for sensing the quality of material or production steps being controlled, with said sensing means coupled to error correcting means for eliminating any detected fault in the production system. The sensitivity of the sensing means is subject to adjustment to regulate the quality limits beyond which error correction is required. It is found that often faults occur which can be tolerated if of a short duration. The equipment however merely senses the magnitude of the fault and actuates the error correcting facilities without regard to the duration of the fault. As a result, error correction often occurs without being necessary, since short duration faults may often be tolerable, and the error correcting operation may produce a defect worse than the short duration fault.

In the textile industry quality control equipment of different types have been evolved. Thus yarn cleaners of great sophistication are now employed to solve problems which until recently were not even recognized. One such problem is to make it possible to detect so called spinner's doubles in yarns and to initiate suitable corrective operations for removing them. Such spinner's doubles may be formed, for example, when the thread balloons of adjacent spinning spindles cross each other and become caught up with each other with the result that the stronger thread tears off the weaker thread and carries the weaker thread with it to be wound on the spool. Spinner's doubles or the so called coarse threads may also occur when two rovings unite on a spinning machine and are thus spun together. If such double threads are not discovered in time, further processing of these threads may lead to considerable loss of quality and expensive loss of material.

Electronic yarn cleaners employ a sensing element to produce an electric signal which is proportional to the cross-section of the yarn and which is representative of the quantity of yarn within a given measured length. Corrective action or cleaning is started when this signal exceeds predetermined limits, which are adjustable according to the desired yarn quality.

In general, it is necessary to remove faults which are only a few centimeters in length, but the cross-section of which is many times the nominal cross-section of the yarn. The above described spinner's doubles have the property that on entering the sensing element, they represent a mean increase of twice the cross-section of the single yarn. The electric signal accordingly also shows a more or less rapid doubling of its amplitude. If the response limits of the yarn cleaner are now adjusted to respond to a signal indicating a double, then all other changes in cross-section of such magnitude will cause the corrective action of the cleaner to be initiated. This would lead to an excessive number of stoppages because faults of double the cross-section but only a few centimeters in length are very frequent and their replacement by a knot is too costly. Moreover, a knot may in many cases be more disturbing than a cross-sectional increase of 100% extending over a short length.

It is with the above problems and desiderata in mind that the present means, including both method and apparatus have been evolved, means regulating the operation of electronically operated quality control equipment such as electronic yarn cleaners so that corrective action is initiated only when a fault occurs over a period of given duration.

It is accordingly among the primary objects of this invention to provide means for regulating the operation of quality control equipment to permit ready adjustment of the equipment to effect correction of only undesired faults.

Another object of the invention is to provide means for regulating the operation of quality control equipment so that it is responsive to both the magnitude and duration of a sensed defect in the controlled system or its production.

A further object of the invention is to provide means permitting regulation of quality control equipment to permit the occurrence of flaws of minor duration or infrequent occurrence, while correcting like flaws when their duration or frequency of occurrence exceeds a selected limit.

It is also an important object of this invention to provide means for regulating the operation of an electronic yarn cleaner to permit the passage of yarn thickenings in short lengths of the processed yarns, but to initiate corrective cleaning action when these thickenings extend over an undesired length of the yarn.

These and other objects of the invention which will become hereinafter apparent are achieved by combining with the quality control equipment such as an electronic yarn cleaner having a sensing element producing a signal representative of the controlled quality of the system such as yarn thickness, means to which said signal is fed which delay the passage of the signal unless it is of given magnitude and duration. The means comprise at least two channels to which the signal is fed. These channels are selectively tuned to accommodate fault indicating input signals from the sensing element indicative of a given fault to be eliminated and to pass an error correcting output signal when a limiting value to which the channel has been timed is exceeded. This output signal is employed to energize error correcting facilities such as a cutting device or the like.

A feature of the invention is that the channels may be tuned to pass an output, or error correcting signal, only when the fault indicating signal has continued over a given period, so that faults of short duration or infrequent occurrence may be ignored if desired.

The specific details of the invention and their mode of functioning will be made most manifest and particularly pointed out in conjunction with the accompanying drawings, wherein.

Referring now more particularly to the drawings, like numerals in the various FIGS. will be employed to designate like parts.

Figure 1:
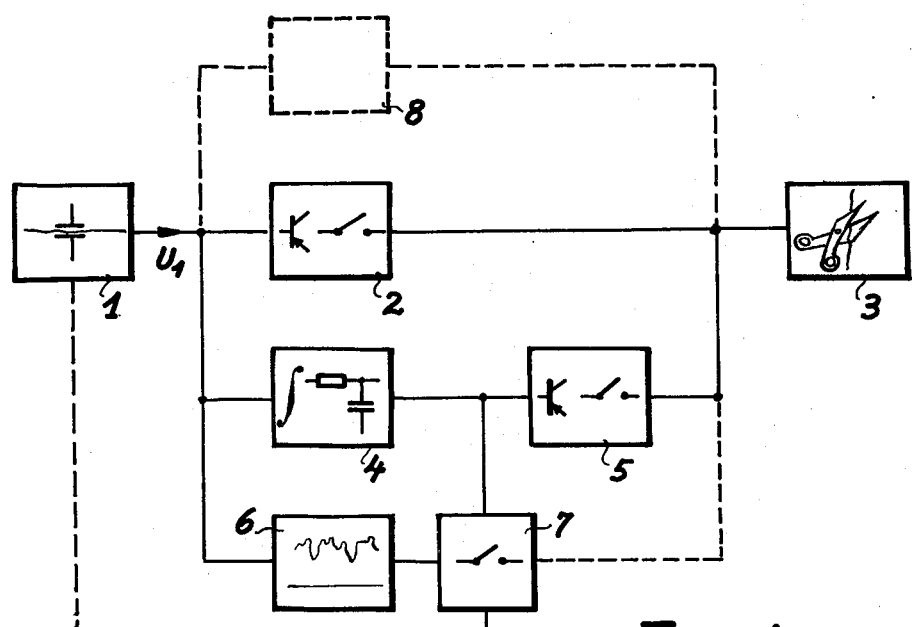
FIG. 1 is a schematic block circuit diagram showing the circuit components required to effect desired quality control regulation.

The circuit shown in FIG. 1 includes a fault detecting sensing element 1, a threshold switch 2, an error correcting cutting device 3, an integrating member 4, a threshold switch 5, a control device 6 and a gate switch 7. The circuit is illustrated as applied to quality control equipment such as a yarn cleaner.

The cross-section or diameter of the yarn passing through the sensing element 1 is converted into an electrical factor, for example a voltage $U_1$. The threshold switch 2 responds when a desired voltage is exceeded and releases the cutting device 3. The elements 1, 2 and 3 thus represent nothing other than the action of known yarn cleaners such as shown by U.S. Pat. Nos. 3,009,101 and 3,039,051.

The voltage $U_1$ is supplied to an integrating member 4, e.g. a low pass filter. The voltage pulses resulting from large, but brief, thickenings cannot pass through the low pass integrating filter 4, whereas a thickening extending over a greater length produces a more prolonged voltage increase which can easily pass the low pass filter 4 and actuate the threshold switch 5. The threshold switch 5 thus responds shortly after the occurrence of a spinner's double in the sensing element 1, but not when short thickenings occur.

A first control is arranged after the sensing element 1, this control acting on the voltage $U_1$, and a second control is provided which acts on the voltage supplied to the threshold switch 2 or on the switch itself. It is thus possible to adjust the yarn count by means of the first control (count control) and to adjust the relative degree of sensitivity to short thickenings by means of the second control (percentage control).

When a yarn is inserted in the sensing element 1, the same voltage increase occurs at the output of the low pass filter 4 as occurs in response to a spinner's double. To prevent actuation of the threshold switch 5 in such cases, control means 6 are provided to actuate a switch 7 as soon as the voltage $U_1$ begins to vary as a result of the variations in yarn cross-section which occur for short periods, for example the switch 7, is closed when the voltage $U_1$ is constant (when no more yarn runs through the measuring element 1) and is opened by the variation of $U_1$ (as the yarn runs through). The condition that the cutting device 3 should not respond when a yarn is inserted, but should respond to the presence of a spinner's double is thus met when the closed switch 7 prevents any actuation of the cutting device 3. This effect may also be obtained when the closed switch 7 either directly influences the threshold switch 5 or the measuring element 1 and hence the voltage $U_1$ or also the voltage at the output end of the low pass filter 4. On the other hand, the switch 7 exerts no effect on the elements 4, 5 and 3.

However, the said condition only partly meets the requirements in practice, because spinner's doubles and coarse threads tend to be relatively long, so that if the spinner's double is cut at its beginning, the remaining fault, from which the beginning has been cut off, may accidentally be knotted to the end of the single thread so that the remaining fault is wound on the spool. To prevent this, it is necessary to provide that the cutting device 3 again responds when the knotted spinner's double is inserted. This is not achieved if the switch 7 prevents any actuation of the cutting device 3. However, it can be achieved by altering the voltage conditions on the threshold switch 5 in such a way that the switch responds when a spinner's double is inserted, but not when a single thread is inserted. This may be done by raising the threshold value of the switch 5 or reducing the voltage at the input to the threshold switch, by reducing the alternating voltage at the output end of the low pass filter 4 or by lowering the direct voltage at the input of the threshold switch 5.

Summarizing, by the above described combination spinner's doubles will be cut as they occur in the yarn, but nothing happens when a single thread is inserted although the cutting device responds when a spinner's double is inserted.

So far, only single yarns and spinner's doubles have been mentioned. However, similar requirements have to be met in the case of twist yarns. The nominal count (2, 3, . . . ) of the twisted threads has to be considered in place of the single thread, and any thread erroneously added thereto is to be counted as a double thread. For example, when cleaning a double twist, the cutting device must respond in the presence of a third thread. The requirements in the cleaning of twist yarns may be met by the present invention by suitable choice of control setting.

Additional means 8 which are selective to other properties of the yarn may be inserted on the path from the measuring device 1 to the cutting device 3. Thus, the means 8 may, for example, comprise a low pass filter and a threshold switch which responds when a thread in a twist yarn is missing or when a single yarn is below the nominal thickness over some length. In this case, the threshold switch must respond as the voltage drops.

The present invention lies in a novel combination of means that are substantially already known. The description of the individual means may therefore be kept very brief.

Any means suitable for the continuous measurement of yarn may be used as the sensing device 1. Optical and capacitative measuring systems such as shown by U.S. Pat. No. 3,039,051 are particularly well known for this purpose. An amplifier connected to such a system is also known. These parts therefore require no further explanation, except to mention that the control of the output voltage $U_1$ (with the count control) may be effected both by controlling the amplification and by controlling the power supply factor of the measuring element (i.e. in an optical system, for example, the brightness of the illumination means or in capacitative systems the amplitude of the HF voltage).

The threshold switch 2 may, for example, be a known "Schmitt"-trigger. The control by means of the percentage control may act both on the threshold value of the threshold switch and on the entering signal or on both. The threshold switch may have filters connected in series with it, e.g. a low pass filter with a fairly high limiting frequency for exclusively suppressing very short voltage peaks which are produced by thickenings which exceed the selected limiting value for cleaning but are best left in the yarn owing to their short length.

Cutting devices 3 are also already known (e.g. shears or knives). Pre-amplifiers and elements possibly provided for limiting the time of the impulses also require no special explanation.

Figure 5:
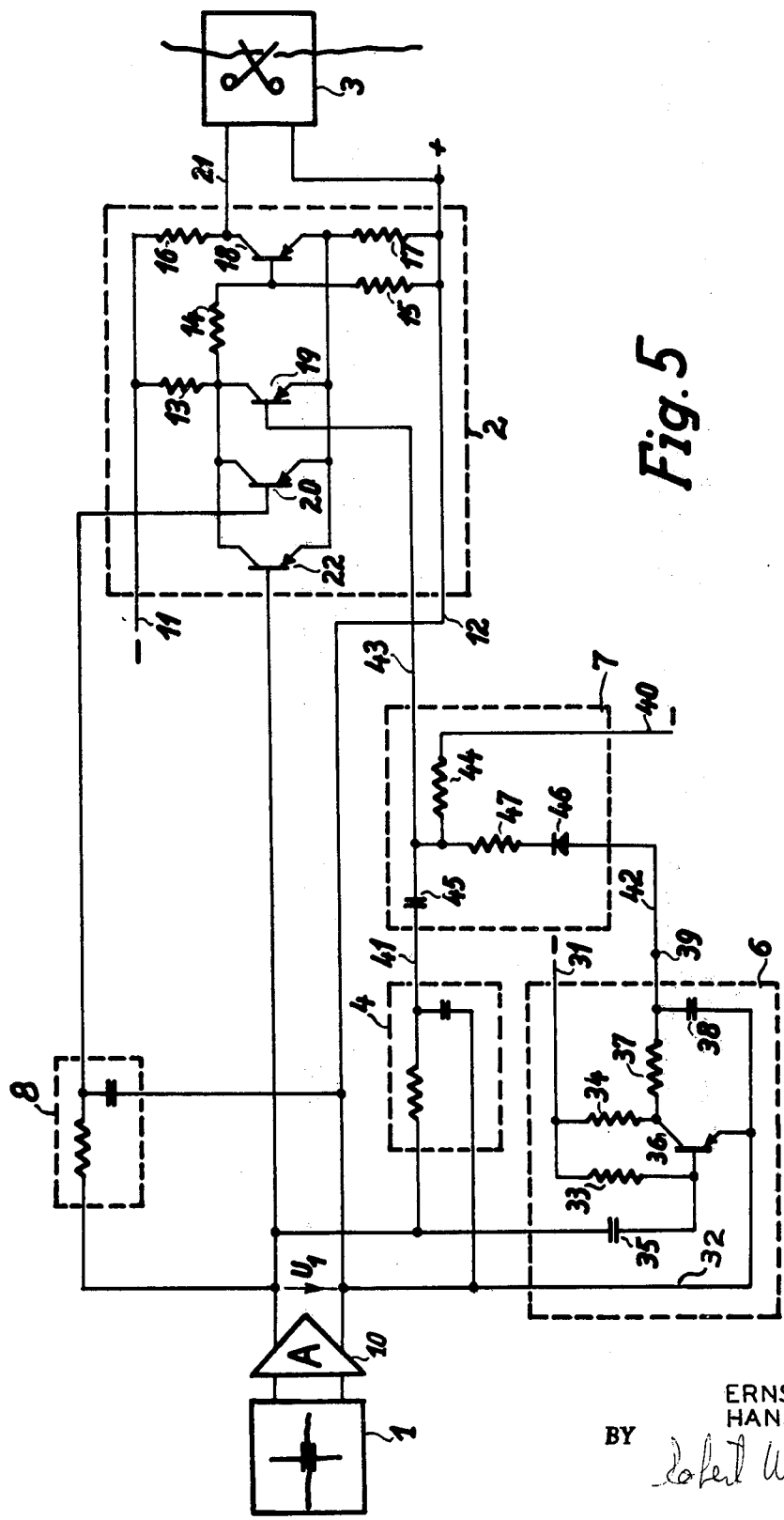
FIG. 5 is a circuit diagram illustrating how the circuit components shown in FIGS. 2 – 4 may be combined to practice the invention.

The integrating member 4 may consist of a single RC member as shown in FIG. 5 which acts as low pass filter and whose limiting frequency is so chosen that voltage fluctuations produced by brief fluctuations in the cross-section, with wavelengths corresponding to 2 to 3 times the staple length of the fibers of which the yarn is formed, are unable to pass.

The threshold switch 5 may be constructed in the same way as the threshold switch 2. If desired, it may be combined with the threshold switch 2 as shown in FIG. 5 in such a way that the switches have separate inputs but a common output. A detailed circuit arrangement for this is shown by way of example in FIG. 2. The feed voltage of the Schmitt trigger lies across the terminals 11 and 12. It can be used for controlling the threshold level. The resistors 13, 14, 15, 16 and 17 together with the transistors 18 and 19 form a known Schmitt trigger in which the base of the transistor 19 forms the input and the collector of the transistor 18 forms the output. The base of the transistor 20 now serves as a further independent input whilst the output at the collector of the transistor 18 acts as a common output. However, additional transistors 22 etc. may be provided so that, for example, the means 8 may be connected to the Schmitt trigger with several independent inputs and one common output.

This results in an apparatus in which the measuring element together with any associated amplifier and control can be used together with the cutting device 3 and its associated elements and a part of the threshold switch.

Figure 3:
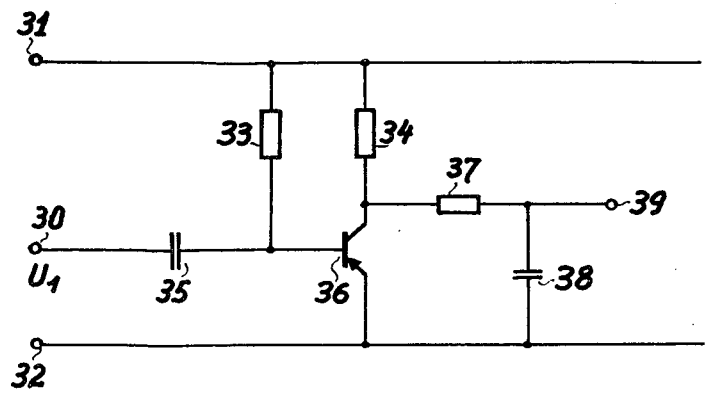
FIG. 3 is a circuit diagram of a control device which may be employed in the FIG. 1 circuit.

The control circuit 6 which actuates the switch 7 may, for example, have the circuit arrangement shown in FIG. 3. The power supply voltage is applied to the terminals 31 and 32. The transistor 36 is non-conductive because the resistor 33 constantly takes current from the base. The collector voltage is thus practically zero. These conditions are stable as long as the voltage $U_1$ is constant, which is the case if the thread is at rest or no thread is inserted, but as soon as the thread is moved through the measuring element 1, the voltage $U_1$ begins to vary. If the voltage increases in the negative direction, a current flows through the condenser 35, and the same current flows through the base of transistor 36. The transistor 36 therefore remains non-conductive and the condenser 35 is charged up because the base of the transistor 36 can at the most have a small negative value. However, as soon as the voltage $U_1$ rises in the positive direction, the base of the transistor 36 becomes positive, the collector-emitter path is opened and the condenser 38 is charged up through the resistors 34 and 37. This condition is maintained as long as the voltage $U_1$ rises more rapidly than the condenser 35 is discharged through the resistor 33. If this rise slows down or becomes negative again, then the collector-emitter path again becomes conductive and the condenser 38 begins to discharge through the resistor 37. However, if a thread is passing through the measuring element 1, this discharge will not be complete, since the change of the increase of the voltage $U_1$ in the negative and positive direction takes place relatively quickly so that at least a certain minimum voltage is retained across the condenser 38. The switch 7 is actuated by this voltage.

Figure 4:
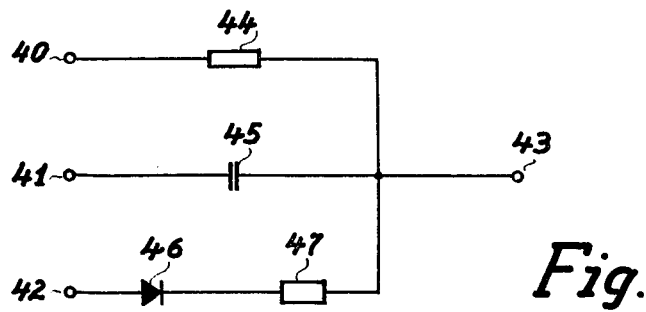
FIG. 4 is a circuit diagram of a gate switch of the type which may be employed in the FIG. 1 circuit.

The switch 7 may have many different forms. It may be either electro-mechanical (e.g. a relay) or an electronic switch. FIG. 4 shows an example of a circuit arrangement of such a switch which is particularly suitable for the invention.

OPERATION

Prior to the description, a number of concepts relating to a threshold switch will now be defined for the sake of clarity: "Threshold Voltage" is that voltage at which the threshold switch responds; "Resting Voltage" is the voltage in the static state at the input of the threshold switch; the "Threshold Value" is the difference between the threshold voltage and the resting voltage.

Figure 2:
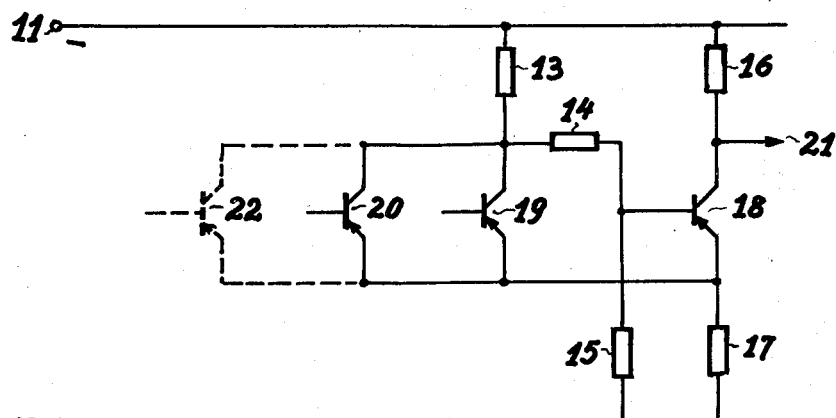
FIG. 2 is a circuit diagram of a threshold switch which may be employed in connection with the arrangement shown in FIG. 1.

The input of the Schmitt trigger according to FIG. 2 is connected to the terminal 43. A direct voltage which is preferably at least about half the threshold voltage and corresponds to the resting voltage when the diode 46 is blocked, is supplied to the terminal 40. The output of the integrating member 44 is connected to the terminal 41. The condenser 45 together with the resistor 44 must have a small limiting frequency. If the signal of a spinner's double now reaches the output of the integrating member 4, the switching voltage must be reached at the terminal 43, i.e. the count control must be suitably adjusted. Finally, the terminal 39 of the control device 6 in FIG. 3 is connected to the terminal 42.

So far it has been assumed that the diode 46 is blocked. This is in fact the case when the potential at the terminal 42 is more negative than the potential at the terminal 43. This is achieved by the circuit arrangement of FIG. 3 described above, when the thread moves through the measuring element 1. If this is not the case, then the potential at the terminal 32 and 42 is practically zero. The potential at the terminal 43 therefore also becomes smaller than that at the terminal 40, i.e., the resting voltage is reduced and the threshold value is therefore increased. When the yarn is inserted, the threshold value is no longer reached, so that an unwanted cutting operation is not released. If, on the other hand, a spinner's double is inserted, then the signal potential at the terminal 41 is greater than in the presence of a single yarn, so that the threshold value is exceeded and the cutting process is released.

The switch 7 may also act on the amplification of the signal voltage at the output of the low pass filter 4 such that the amplification e.g. for spinner's doubles is reduced to about half. The cutting device is therefore correctly released when a spinner's double is inserted but not when a single yarn is inserted.

An example of an operative circuit embodying the invention is shown in FIG. 5. In this circuit, the signal $U_1$ from sensing element 1 and amplifier 10 is fed to threshold switch 2, in which it controls a transistor 22. Connected in parallel to the output of amplifier 10 is integrating member 4 and control device 6; as well as additional integrating means 8. The signals from integrating member 4 are fed to transistor 19 of threshold switch 2, and the signal from additional integrating means 8 controls the base of transistor 20 in threshold switch 2. Therefore, threshold switch 5 of FIG. 1 is incorporated in threshold switch 2. Control device 6 as in FIG. 3 is in parallel to the output of the amplifier 10 and to the integrating member 4. It controls switch 7, the function of which is disclosed in connection with FIG. 4, whereby the switch 7 controls transistor 19 in the threshold switch 2 and, as a consequence, also cutting device 3.

Some specific values of the circuit components of FIG. 5 are give below.

| 1. Potentials: | 11 and 31 | −20 Volts |
|---|---|---|
| | 12 | Zero Volts |
| | 40 | Variable |
| 2. Resistors: | 13 | 1 kOhms |
| | 14 | 1 " |
| | 15 | 1 " |
| | 16 | 1 " |
| | 17 | 1 " |
| | 33 | 100 kOhms |
| | 34 | 10 " |
| | 37 | 10 " |
| | 44 | 100 " |
| | 47 | 10 " |
| | in frame 4 | 10 kOhms |
| | in frame 8 | 10 " |
| 3. Capacitors: | 35 | 10 MFarads |
| | 38 | 10 " |
| | 45 | 100 " |
| | in frame 4 | 10 MF |
| | 8 | 1 MF |

It is thus seen that simple effective means have been provided for regulating the operation of quality control equipment so that corrective action is initiated only when flaws of given magnitude and given duration or frequency of occurrence are sensed.

The above disclosure has been given by way of illustration and elucidation, and not by way of limitation, and it is desired to protect all embodiments of the herein disclosed inventive concept within the scope of the appended claims.

What is claimed is:

1. A method for regulating the operation of yarn clearers having error correcting means such as yarn cutters, and sensing means providing an electrical signal representative of the controlled quality, said method comprising the steps of: feeding the signal from the sensing means to two independent electrical circuit channels each having separate threshold switch means, the threshold switch means of one circuit responsive to signals corresponding to yarn faults of given magnitude, the threshold switch means of the other circuit responding to signals corresponding to faults of given duration; and obtaining an independent control signal from each of said channels for initiating the operation of the cutters when a limiting value selected for each of said two channels is exceeded.

2. A method according to claim 1 for controlling yarn quality wherein one channel responds to a signal indicative of the mean cross-section of a predetermined length of the yarn, and the limiting value is selected such that the control signal is given as soon as the said cross-section whose mean value is taken over a given length exceeds a desired yarn count.

3. A method according to claim 2, wherein the electrical signal representative of the controlled quality is fed to a control device which responds to variations of the electrical signal to prevent a signal being passed on the insertion of yarn into the measuring element.

4. A method according to claim 1, wherein the control device is arranged to act on the input signal to a threshold switch so that when a yarn having the nominal yarn count is inserted in the measuring element, the threshold switch does not give a signal while it does give a signal when the cross-section, whose mean value determined over a given length, varies from the nominal yarn count.

5. A method according to claim 1, wherein the signal in one of said channels is integrated to provide an output voltage which is reduced to such an extent by the control device that a threshold switch does not give a signal when yarn having the nominal yarn count is inserted in the measuring element but does give a signal when the mean cross-section, determined over a given length exceeds the nominal yarn count.

* * * * *